(12) United States Patent
Boussignac

(10) Patent No.: US 6,415,787 B1
(45) Date of Patent: Jul. 9, 2002

(54) DEVICE FOR CHANGING RESPIRATORY PROBES IN THE TRACHEA OF A PATIENT

(76) Inventor: Georges Boussignac, 1, Avenue de Provence, Antony (FR), 91260

(*) Notice: Subject to any disclaimer, the term of this patent is extended or adjusted under 35 U.S.C. 154(b) by 0 days.

(21) Appl. No.: 09/125,971
(22) PCT Filed: Jan. 5, 1998
(86) PCT No.: PCT/FR98/00003
§ 371 (c)(1),
(2), (4) Date: Aug. 28, 1998
(87) PCT Pub. No.: WO98/30264
PCT Pub. Date: Jul. 16, 1998

(30) Foreign Application Priority Data

Jan. 6, 1998 (FR) .............................. 97 00043

(51) Int. Cl.⁷ ............................................ A61M 16/00
(52) U.S. Cl. ........................... 128/200.26; 128/207.14; 128/207.15
(58) Field of Search ....................... 128/200.26, 207.14, 128/207.15, 207.16, 207.17, 207.18, DIG. 22; 607/264, 523, 524, 525, 526

(56) References Cited

U.S. PATENT DOCUMENTS

| | | | | |
|---|---|---|---|---|
| 2,936,761 A | * | 5/1960 | Snyder | 604/523 |
| 3,802,440 A | * | 4/1974 | Salem et al. | 128/200.26 |
| 3,814,091 A | * | 6/1974 | Henkin | 128/204.18 |
| 4,051,847 A | * | 10/1977 | Henkin | 128/204.18 |
| 4,244,362 A |   | 1/1981 | Anderson | |
| 4,275,724 A | * | 6/1981 | Behrstock | 128/207.14 |
| 4,300,550 A | * | 11/1981 | Gandi et al. | 128/207.18 |
| 4,406,656 A | * | 9/1983 | Hattler et al. | 604/280 |
| 4,571,239 A | * | 2/1986 | Heyman | 604/54 |
| 4,607,635 A | * | 8/1986 | Heyden | 128/207.15 |
| 4,672,960 A | * | 6/1987 | Frankel | 128/200.26 |
| 4,685,457 A | * | 8/1987 | Donenfeld | 128/207.14 |
| 4,717,379 A | * | 1/1988 | Ekholmer | 604/43 |
| 4,735,620 A | * | 4/1988 | Ruiz | 604/281 |
| 4,819,664 A | * | 4/1989 | Nazari | 128/207.15 |
| 4,825,585 A | * | 5/1989 | Frankel | 128/200.26 |
| 4,840,172 A | * | 6/1989 | Augustine et al. | 128/207.14 |
| 4,846,814 A | * | 7/1989 | Ruiz | 604/281 |
| 4,865,586 A | * | 9/1989 | Hedberg | 604/93 |
| 4,892,095 A | * | 1/1990 | Nakhgevany | 128/207.14 |
| 4,898,168 A | * | 2/1990 | Yule | 128/207.15 |
| 4,960,122 A |   | 10/1990 | Mizus | |
| 4,961,731 A | * | 10/1990 | Bodicky et al. | 604/264 |
| 5,052,386 A |   | 10/1991 | Fischer, Jr. | |
| 5,058,577 A | * | 10/1991 | Six | 128/200.26 |
| 5,119,811 A | * | 6/1992 | Inglis et al. | 117/207.14 |
| 5,186,167 A | * | 2/1993 | Kolobow | 128/207.14 |
| 5,201,310 A | * | 4/1993 | Turnbull | 128/207.15 |
| 5,203,320 A | * | 4/1993 | Augustine | 128/200.26 |
| 5,235,970 A | * | 8/1993 | Augustine | 128/200.26 |
| 5,257,620 A | * | 11/1993 | Schermerhorn | 128/200.26 |
| 5,257,636 A | * | 11/1993 | White | 128/200.26 |
| 5,359,999 A | * | 11/1994 | Kinsmen | 128/204.21 |
| 5,364,356 A | * | 11/1994 | Hofling | 604/96 |
| 5,385,563 A | * | 1/1995 | Gross | 604/284 |

(List continued on next page.)

FOREIGN PATENT DOCUMENTS

WO    WO 90/04992    5/1990

Primary Examiner—John G. Weiss
Assistant Examiner—Joseph F. Weiss
(74) Attorney, Agent, or Firm—Fisher, Christen & Sabol

(57) ABSTRACT

A tubular, flexible and elongate device, which has at least one distal orifice and at least one proximal orifice, for replacing a respiratory probe which is already in place in the trachea of a patient, and which is supplied with respiratory assistance gas via at least one main supply conduit with another respiratory probe external to the patient. The device may be introduced into both of the respiratory probes, and may be connected via its proximal orifice to an auxiliary conduit for supplying respiratory gas at a higher pressure than that of the main supply conduit.

2 Claims, 6 Drawing Sheets

U.S. PATENT DOCUMENTS

| | | | | |
|---|---|---|---|---|
| 5,404,873 A | * | 4/1995 | Leagre et al. | 128/204.18 |
| 5,425,723 A | * | 6/1995 | Wang | 604/280 |
| 5,560,351 A | * | 10/1996 | Gravenstein et al. | 128/200.26 |
| 5,582,167 A | * | 12/1996 | Joseph | 128/207.15 |
| 5,590,644 A | * | 1/1997 | Rosenkoetter | 128/201.13 |
| 5,593,394 A | * | 1/1997 | Kaneska et al. | 604/282 |
| 5,603,694 A | * | 2/1997 | Brown et al. | 604/49 |
| 5,718,678 A | * | 2/1998 | Fleming, III | 604/43 |
| 5,746,202 A | * | 5/1998 | Pagan | 128/207.14 |
| 5,749,357 A | * | 5/1998 | Linder | 128/200.26 |
| 5,778,872 A | * | 7/1998 | Fukunaga et al. | 128/202.27 |
| 5,819,723 A | * | 10/1998 | Joseph | 128/207.14 |
| 5,827,242 A | * | 10/1998 | Follmer et al. | 604/282 |
| 5,873,858 A | * | 2/1999 | Schafer et al. | 604/161 |
| 5,873,865 A | * | 2/1999 | Horzewski et al. | 604/280 |
| 5,882,346 A | * | 3/1999 | Pomeranz et al. | 604/280 |
| 5,882,347 A | * | 3/1999 | Mouris-Laan et al. | 604/280 |
| 5,906,593 A | * | 5/1999 | Schafer et al. | 604/161 |
| 5,919,183 A | * | 7/1999 | Field | 604/530 |
| 5,964,223 A | * | 10/1999 | Baran | 128/207.14 |
| 5,980,516 A | * | 11/1999 | Mulier et al. | 606/41 |
| 5,989,230 A | * | 11/1999 | Frassica | 604/264 |
| 5,997,497 A | * | 12/1999 | Nita et al. | 604/22 |
| 6,027,516 A | * | 2/2000 | Kolobow et al. | 606/191 |
| 6,053,900 A | * | 4/2000 | Brown et al. | 604/500 |

* cited by examiner

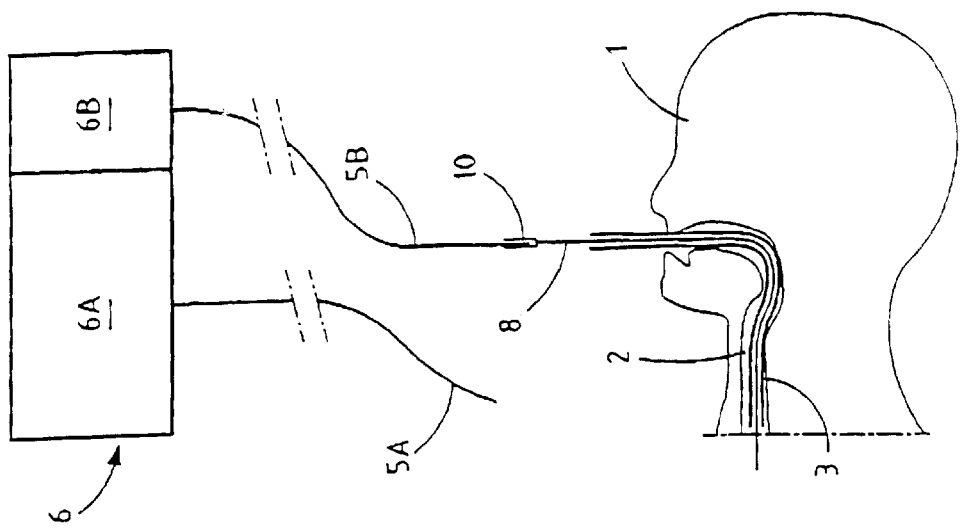
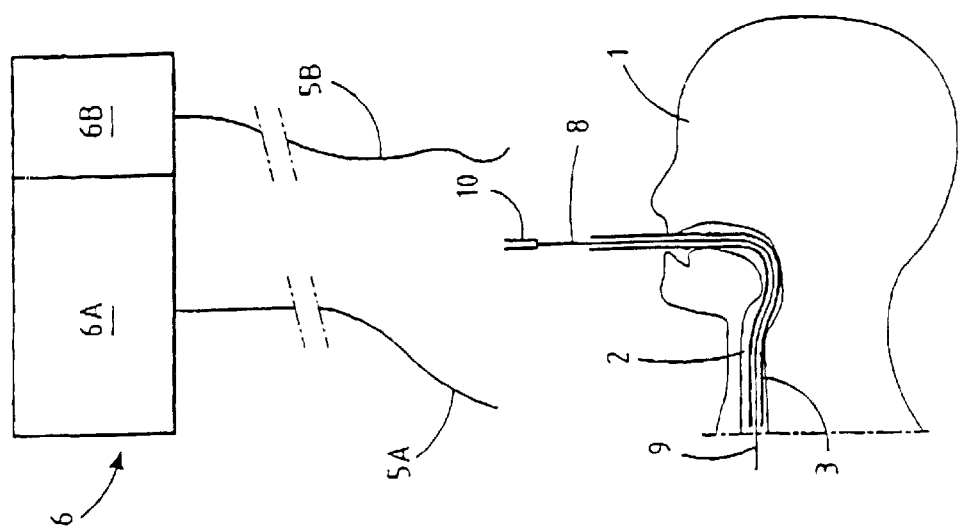
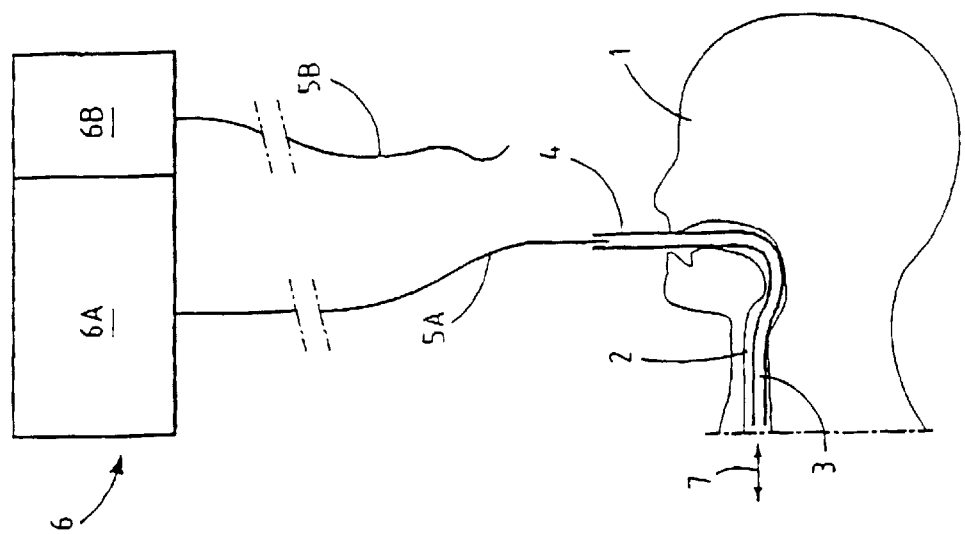

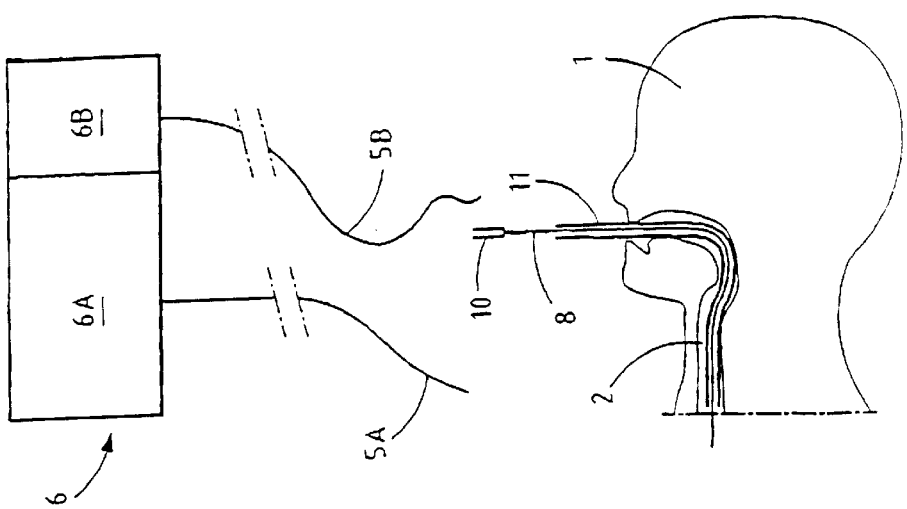
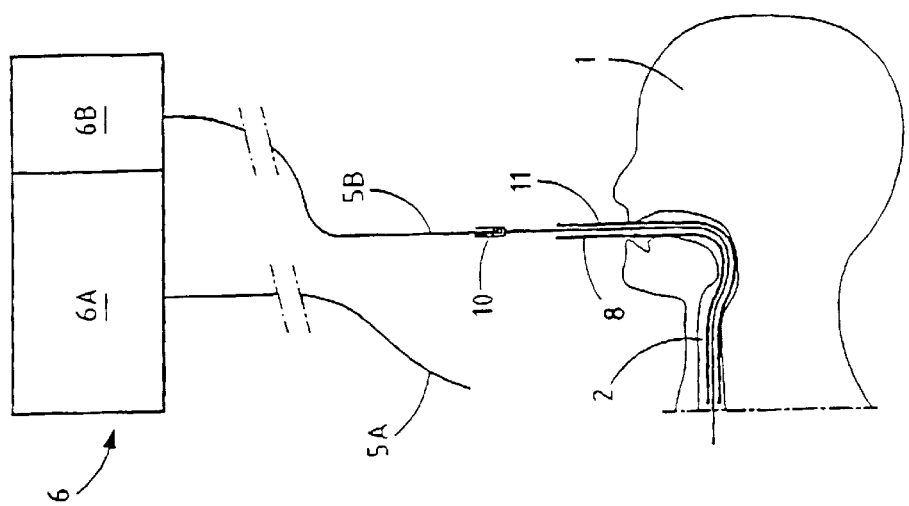
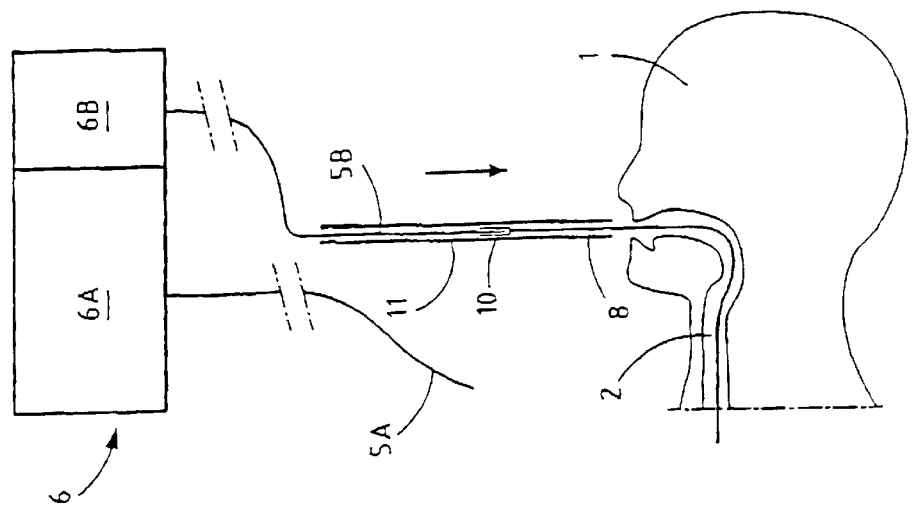

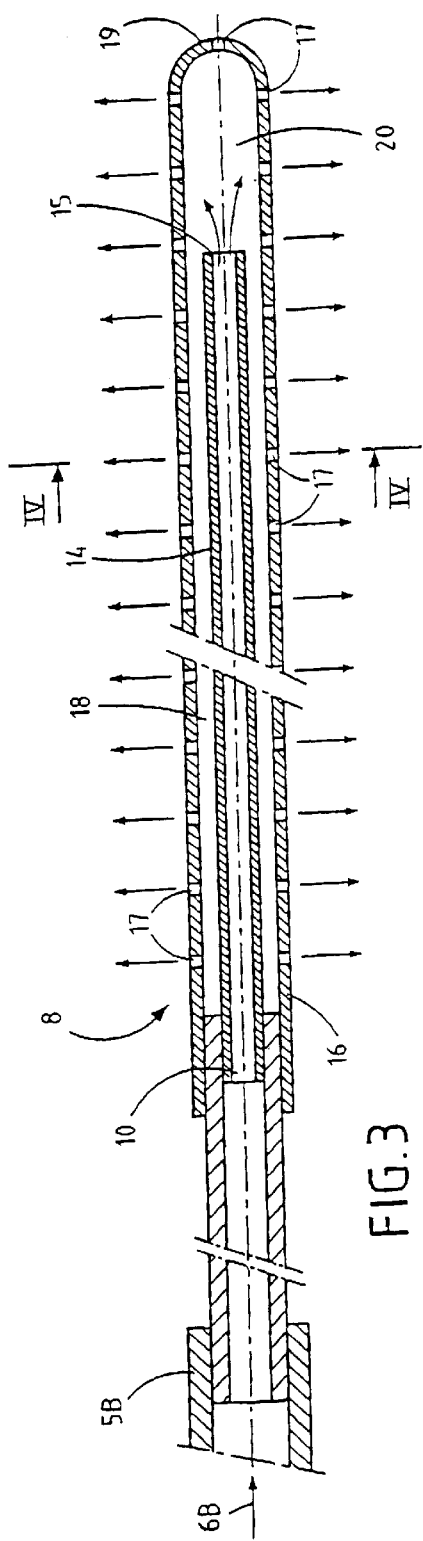
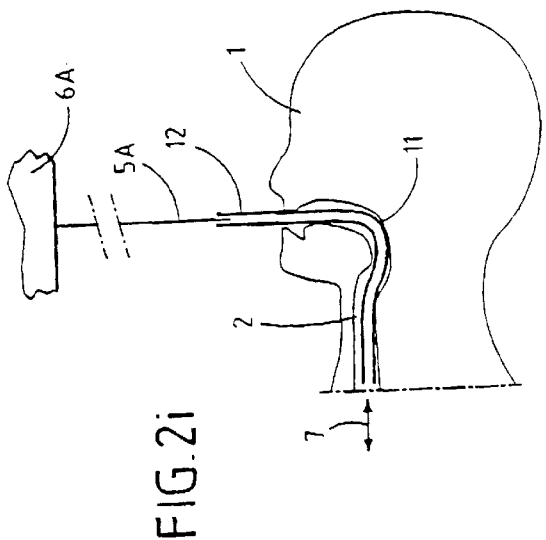
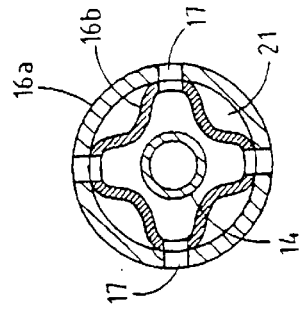
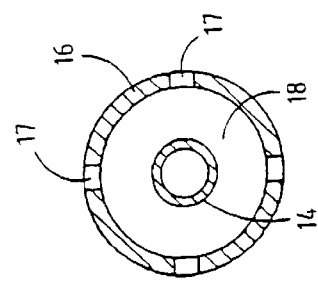
FIG.3
FIG.2i
FIG.5
FIG.4

DEVICE FOR CHANGING RESPIRATORY PROBES IN THE TRACHEA OF A PATIENT

The present invention relates to a device with which it is possible to replace a first respiratory probe, for example a used one already in place in the trachea of a patient, with a second respiratory probe, for example a new one, external to said patient.

It is known that patients requiring respiratory assistance are connected to an appropriate gas source, for example linked up to an artificial respirator.

The patient is provided with a probe, in his trachea, and this probe is connected to said respiratory gas source via at least one supply conduit.

It is also known that for reasons of hygiene or for technical reasons, such a probe has to be replaced from time to time, for example because of the deterioration of some of its components (positioning balloon), or else in order to replace the probe in situ with a probe of a different type. The positioning of a replacement probe is generally a complex and painful operation, because very often the surface of the trachea is swollen and its diameter is reduced.

Moreover, the procedure of replacing one probe with another one necessitates interruption of the respiratory assistance for a relatively long period of time, and this is prejudicial to the health of the patient.

The object of the present invention is to overcome these disadvantages.

To this end, according to the invention, the device for replacing a first respiratory probe, already in place in the trachea of a patient, with a second respiratory probe external to said patient, said first probe being supplied with respiratory assistance gas via at least one main supply conduit, is distinguished by the fact that:

it is tubular, flexible and elongate and has at least one distal orifice and at least one proximal orifice;

it can be introduced into said first and second respiratory probes, which are able to slide on said device; and it can be connected via its proximal orifice to an auxiliary conduit for supplying respiratory gas at a higher pressure than that of the main supply conduit.

Moreover, it is advantageous that said respiratory probes can slide on said auxiliary supply conduit.

Thus, by means of the present invention, the procedure for replacing a first respiratory probe, already in place in the trachea of a patient, with a second respiratory probe external to said patient, said first probe being supplied with respiratory assistance gas via at least one main supply conduit connected to said first probe, can consist in the sequence of the following steps:

a) said main supply conduit is disconnected from said first respiratory probe and said flexible and elongate tubular device having at least one distal orifice and at least one proximal orifice is introduced into said first respiratory probe;

b) said flexible and elongate tubular device is connected via its proximal orifice to said auxiliary conduit for supplying respiratory gas at a higher pressure than that of the main supply conduit;

c) said first probe is withdrawn from said trachea by sliding it along said flexible and elongate tubular device kept in place in the trachea, and, if appropriate, along said auxiliary supply conduit;

d) said auxiliary supply conduit is disconnected from said flexible and elongate tubular device and said first probe is removed;

e) said second probe is passed onto said auxiliary supply conduit, or, if appropriate, onto said flexible and elongate tubular device, and said flexible and elongate tubular device is connected via its proximal orifice to said auxiliary supply conduit; and f) said second probe is slid over said flexible and elongate tubular device until it is correctly positioned in the trachea.

It is therefore possible, by means of the present invention, to minimize the interruption in respiratory assistance since each disconnection of the supply conduits can be of short duration. Moreover, said flexible and elongate tubular device serves as a guide for withdrawing the first respiratory probe and for positioning the second of said probes, which fact facilitates the change of probes and reduces the operating procedure for doing so.

It will be noted, furthermore, that said flexible and elongate tubular device can serve as a guide during the earlier positioning of said first probe. After step f), it could also remain in place in said second probe in order to dispense the respiratory assistance gas to the patient.

However, according to one advantageous embodiment of the procedure described above, after above mentioned step f), the following two additional successive steps are implemented:

g) said auxiliary supply conduit is disconnected from said flexible and elongate tubular device, and said flexible and elongate tubular device is withdrawn from said second probe; and h) said main supply conduit is connected to said second probe.

The device according to the present invention can include:

a central tubular core having a proximal orifice which can be connected to said auxiliary supply conduit and a distal orifice for dispensing said respiratory gas; and a tubular sheath surrounding said tubular core with clearance and made integral with said central tubular core.

At its distal end, said tubular sheath preferably projects from the distal end of said tubular core.

Thus, said central tubular core is protected by said tubular sheath so that the distal orifice of said tubular core cannot be blocked, for example by mucus. For similar reasons, in a first embodiment, said tubular sheath is provided with orifices in its side wall and is closed, at its distal end, by a closure wall, if appropriate provided with one or more orifices.

The length of said device is advantageously such that when it is positioned in the trachea of said patient, said tubular sheath protrudes from the patient's mouth, and that part of said sheath external to said patient is also provided with orifices.

Thus, a dangerous overpressure cannot occur in the trachea of the patient since the respiratory assistance gas is able to escape via the orifices of the sheath external to the patient.

In a second embodiment of said device according to the present invention, the tubular sheath is open at its distal end, and said clearance, between the central core and the sheath, is connected to a source of pressurized fluid, for example a source of water. It is thus possible to humidify the trachea and prevent the latter from drying under the action of the respiratory assistance gas. Of course, any other fluid (medication for example) could be conveyed in this way via said clearance. Moreover, it is possible to provide auxiliary fluid conduits between said sheath and said core, and also, if appropriate, within the wall thickness of these.

Moreover, to avoid the core and the sheath being crushed at the sites of the bends of the device (and thus an interruption in respiratory assistance), and in order to centre said device in relation to the trachea walls, it is advantageous that said device, irrespective of its embodiment, includes an outer helical spring surrounding said tubular sheath. Such a spring can be made of a material with shape memory (Nitinol, for example) and can assume its helical shape only when it is subjected to the temperature conditions prevailing in the trachea.

According to a third embodiment of said device according to the present invention, said central tubular core and said tubular sheath have a helical shape.

In yet another embodiment, the device according to the invention includes an elongate body, made of synthetic material for example, provided with a plurality of longitudinal channels, one of which can be connected to an auxiliary supply conduit for respiratory gas, at its proximal end. In another of said longitudinal channels it is possible to introduce a deformable wire in order to impart its shape, for example its helical shape, to said device.

The figures in the attached drawing will show clearly how the invention can be realized. In these figures, identical references designate similar elements.

FIG. 1 is a diagrammatic view illustrating a patient under assisted respiration.

FIGS. 2a to 2i illustrate the procedure for changing respiratory assistance probes using the device according to the present invention.

FIG. 3 illustrates, in axial longitudinal section, a first embodiment of the device according to the present invention.

FIG. 4 is a cross-section along the line IV—IV in FIG. 3.

FIG. 5 illustrates a variant of the device according to the first embodiment of the present invention, likewise in cross-section similar to FIG. 4.

Figure 2E:
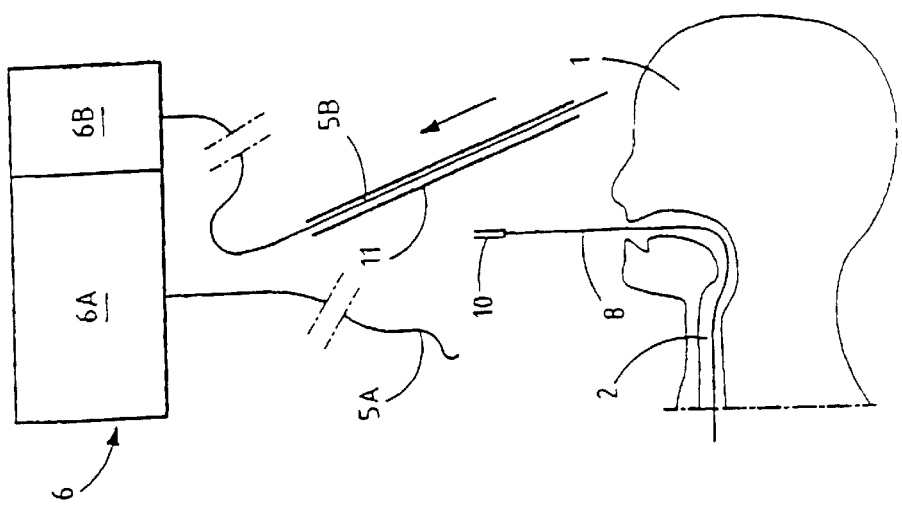

FIG. 1 shows a patient 1 in whose trachea 2 there has been placed a first tubular respiratory probe 3, of which the proximal end 4 protrudes from said patient's mouth. In FIG. 1, the probe is represented in an extremely diagrammatic way, in the form of a simple tube, and the means (such as a balloon) for keeping the probe 3 in place in the trachea 2 have not been represented.

The proximal end 4 of the probe 3 is connected via a supply conduit 5A to an artificial respirator 6A. Thus, the artificial respirator 6A can convey respiratory gas cycles to the lungs of the patient 1 (see arrows 7) at an appropriate pressure.

As can be seen from FIGS. 1 to 2i, the artificial respirator 6A is connected to an auxiliary respiratory gas source 6B in order to form a dual source of gas 6. By way of an auxiliary supply conduit 5B, the auxiliary source 6B delivers respiratory gas at a pressure greater than that delivered by the main conduit 5A.

When the probe is to be replaced, one starts by disconnecting the main supply conduit SA from said first respiratory probe 3, and one introduces into the latter a flexible and elongate tubular device 8, according to the present invention and having at least one orifice at its distal end 9 and at least one orifice at its proximal end 10 (FIG. 2a). The auxiliary conduit 5B is then connected to the orifice at the proximal end of said tubular device 8 in such a way that the interruption in the respiratory assistance of the patient is short and just sufficient to introduce the flexible tubular element into the probe 3 (see FIG. 2b). By virtue of the fact that the pressure of the source 6B is greater than that of the respirator 6A, the respiratory assistance is satisfactory despite the smaller diameter of the tubular device 8.

Then (see FIG. 2c), the first probe 3 is withdrawn from the trachea 2 of the patient by sliding it along said tubular device 8 and said auxiliary supply conduit 5B.

Figure 2D:
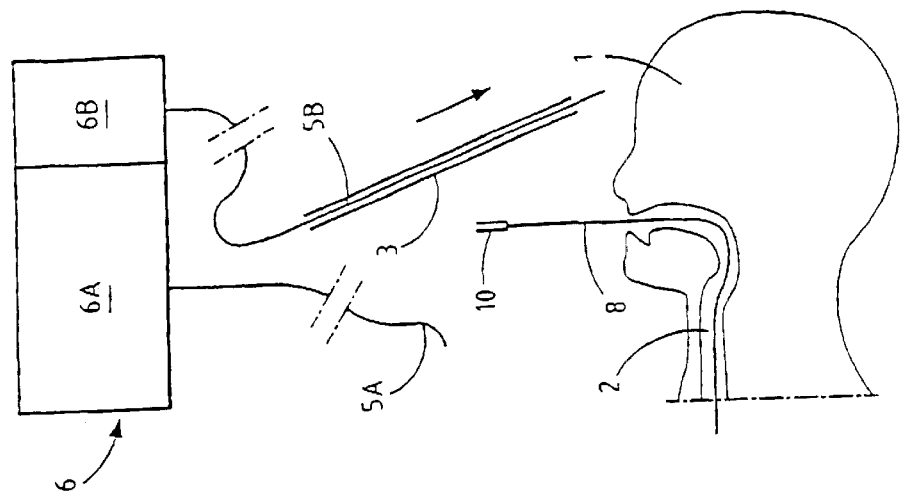
Figure 2C:
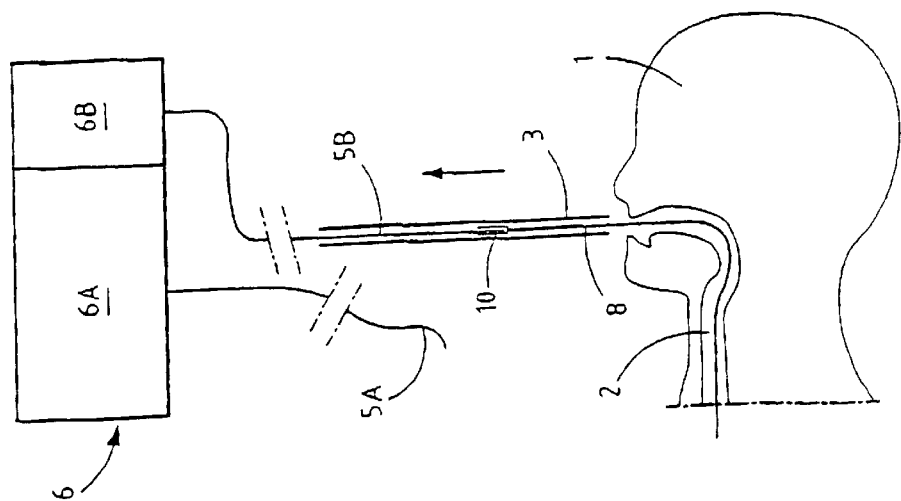

It is then possible (see FIG. 2d) to disconnect the auxiliary conduit 5B from the proximal end 10 of the flexible tubular device 8 and to remove said probe 3. The latter can be replaced with a second probe 11 (FIG. 2e) passed onto said auxiliary conduit 5B. The proximal end 10 of the flexible tubular device 8 is then reconnected to the auxiliary conduit 5B, and the new respiratory probe 11 is slid into the trachea 2 of the patient 1, using said flexible tubular device 8 as a positioning guide (FIG. 2f).

Here, once again, it will be noted that the interruption in respiratory assistance is very short, just sufficient to replace the first probe 3 with the second probe 11 on the auxiliary supply conduit 5B.

Finally (see FIG. 2g), the second respiratory probe 11 is pushed onto the guide 8 until it takes up the position of the first probe 2.

If appropriate, the flexible tubular device 8 is then disconnected from the auxiliary conduit 5B (FIG. 2h), said flexible tubular device 8 is withdrawn, and the main supply conduit 5A is connected to the proximal end 12 of said second probe 11 (FIG. 2i).

In FIGS. 3 and 4, a first embodiment of the flexible and elongate tubular device 8 has been shown. As can be seen, this includes a central tubular core 14 comprising a proximal orifice 10, intended to be connected to the auxiliary conduit 5B for supplying respiratory gas, and a distal orifice 15, intended to dispense the respiratory assistance gas conveyed through the auxiliary supply conduit 5B.

The central core 14 is surrounded by a tubular core 16 provided with orifices 17 in its side wall. Formed between the central core 14 and the tubular sheath 16 there is a space 18 of annular cross-section.

At its distal end, the tubular sheath 16 is closed off by a wall 19, itself provided with orifices 17.

As can be seen, the distal end 15 of the central tubular core 14 is set back relative to the end wall 19 of the tubular sheath 16, so that a chamber 20 is formed between the distal orifice 15 and the wall 19.

Furthermore, the length of the device 8 is such that the orifices 17 which are situated at the proximal end of the sheath 16 are situated outside the patient's mouth when the tubular element 8 is in place in the probes 3 and 11.

Thus, the gas conveyed via the conduit 5 is delivered through the tubular core 14 into the chamber 20, and then from the latter into the annular space 18, and through the orifices 17 towards the patient's lungs.

Of course, although a particularly simple embodiment has been shown in FIGS. 3 and 4, it is possible to complete the tubular device 8 by adding internal channels for the injection of medication, measuring pressure, etc.

FIG. 5 shows an alternative embodiment in which the sheath 16 includes two walls 16a and 16b which are made integral with one another only in proximity to the holes 17, in order to form between them a channel 21 which is intended either to introduce a medicament or to measure pressure, or else for any other use.

The flexible tubular device 8 is preferably made of a synthetic material.

Figure 6:
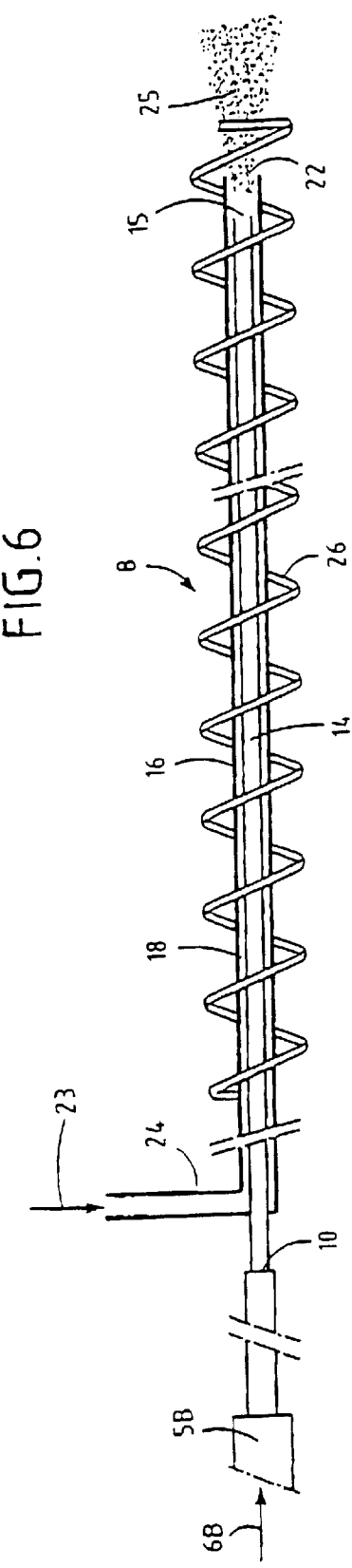
FIGS. 6 and 7 illustrate, in diagrammatic longitudinal views, two other embodiments of the device according to the present invention.

In the second embodiment of the flexible and elongate tubular device 8, shown in FIG. 6, the sheathing 16 is open at its distal end via an orifice 22, and its side wall does not include any orifice 17.

At its proximal end, the space 18 of annular cross-section is connected to a source of pressurized fluid 23, for example water, by way of a connector 24.

Thus, a cloud of atomized water 25, driven by the stream of respiratory assistance gas passing through the core 14, appears at the outlet of the device 8.

Moreover, in order to avoid crushing of the core 14 and of the sheathing 16 at the bends made by the device 8, the latter includes a helical spring 26, integral with at least the proximal end of the sheathing 16 and surrounding the latter. The diameter of the wire of the helix 26 is, for example, of the order of 300 to 600 microns. The helical spring 26 is made, for example, of a material with shape memory, such as that known by the trade name NITINOL.

Figure 7:
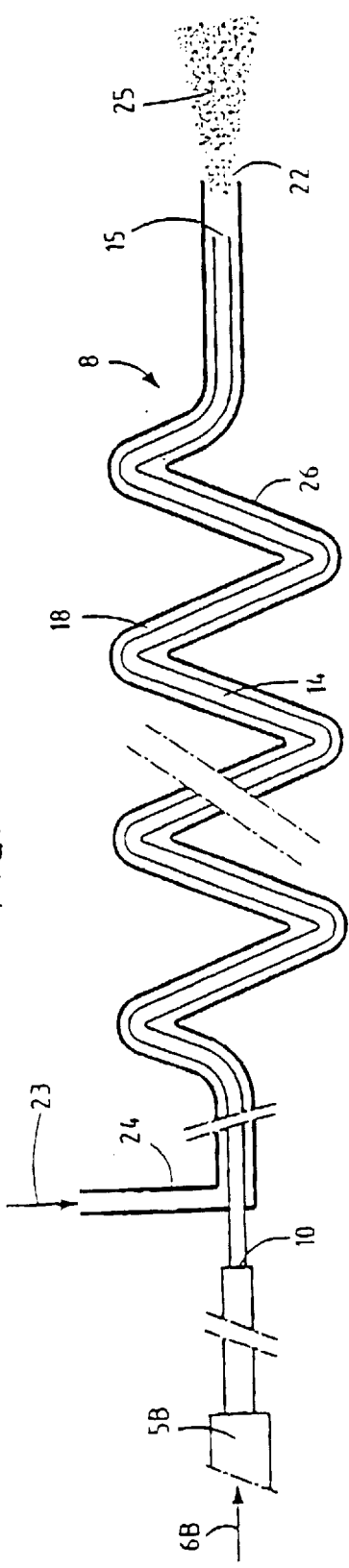
Figure 8:
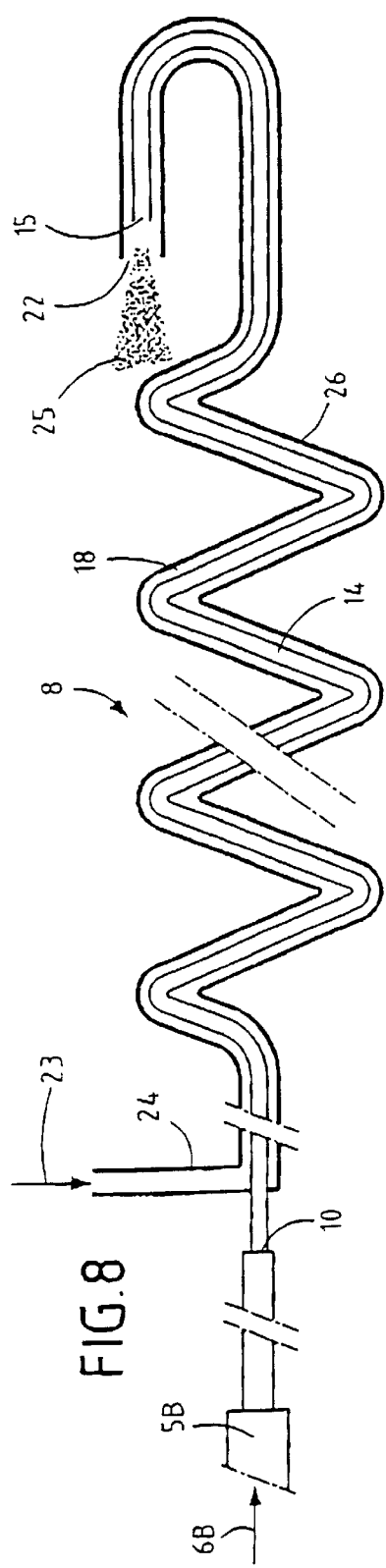
FIGS. 8 and 9 show two variants of the embodiment in FIG. 7.

According to the third embodiment illustrated in FIG. 7, the core 14 and the sheathing 16 each form a helix, the helix of the core 14 being lodged in the helix of the sheathing 16. In this way, the protection against crushing is thus achieved without having to provide a special helical spring 26. It will be noted, as is shown in FIG. 8, that the distal end of the device 8 can have any desired orientation. In this FIG. 8, said distal end is curved back towards the proximal end.

Figure 9:
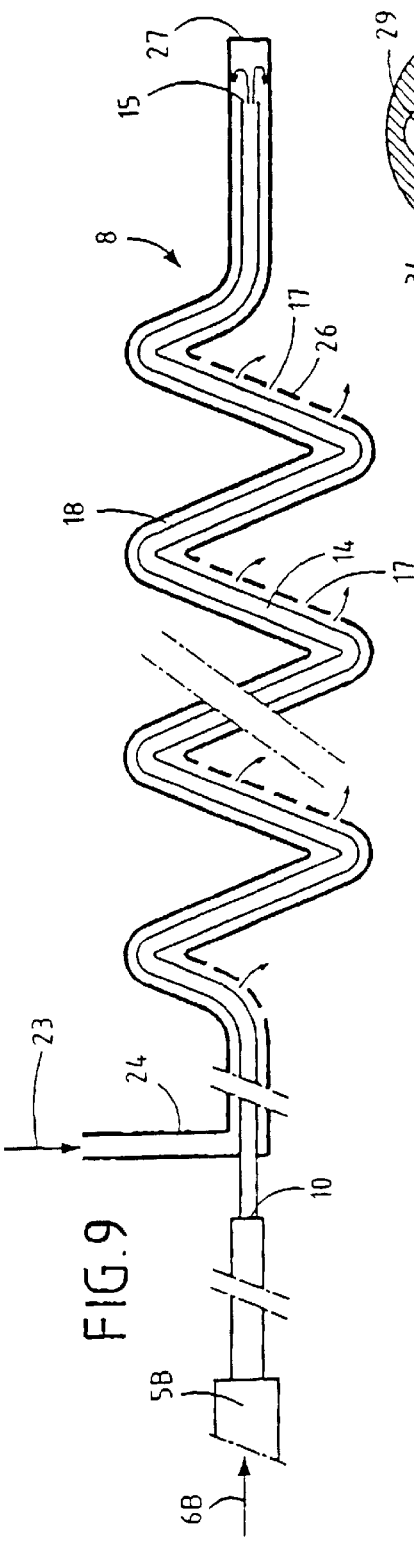

Furthermore, in the alternative embodiment in FIG. 9, the orifice 22 at the distal end of the sheathing 16 is closed by a wall 27, while the wall of said sheathing 16 includes orifices 17 distributed along its length and, for example, directed towards the axis of the helices 14 and 16. The injection of respiration gas is thus distributed along the device 8.

Figure 10:
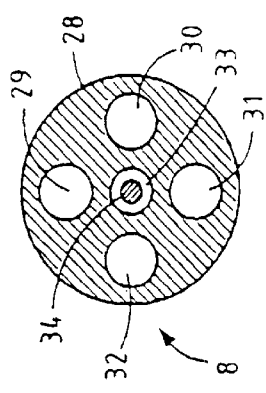
FIG. 10 illustrates, in cross-section, yet another embodiment of the device according to the present invention.

FIG. 10 illustrates, in cross-section, another illustrative embodiment of the elongate body 28 of the device 8. This body 28 includes a plurality of longitudinal channels 29 to 33, of which two can act as the core 14 and the annular space 18 which have been described above. Other longitudinal channels can be used for injecting medicaments, measuring pressure, etc. A last longitudinal channel 33 has a deformable wire 34, for example of metal, passing through it and making it possible to shape said body 28 (for example into a helix).

What is claimed is:

1. A method for replacing a first respiratory probe, already in place in a patient's trachea, with a second respiratory probe external to said patient, said first probe being supplied with respiratory assistance gas via at least one main supply conduit connected to said first probe, wherein the method comprises the following steps:

(a) disconnecting said main supply conduit from said first respiratory probe, and introducing a flexible and elongate tubular device having at least one machine end orifice and at least one patient end orifice into said first respiratory probe;

(b) connecting said flexible and elongate tubular device via its machine end orifice to an auxiliary conduit as a second supply conduit, for supplying respiratory gas which is at a higher pressure than that of the main supply conduit;

(c) withdrawing said first probe from said trachea by sliding it along said flexible and elongate tubular device kept in place in the trachea;

(d) disconnecting said auxiliary supply conduit from said flexible and elongate tubular device and said first probe is removed;

(e) passing said second probe onto said flexible and elongate tubular device, and connecting said flexible and elongate tubular device via its machine end orifice to said auxiliary supply conduit; and (f) sliding said second probe over said flexible and elongate tubular device until it is correctly positioned in the trachea.

2. The method according to claim 1, comprising the further steps:

(g) disconnecting said auxiliary supply conduit from said flexible and elongate tubular device, and withdrawing said flexible and elongate tubular device from said second probe; and (h) connecting said main supply to said second probe.

* * * * *

UNITED STATES PATENT AND TRADEMARK OFFICE
CERTIFICATE OF CORRECTION

PATENT NO.    : 6,415,787 B1
DATED         : July 9, 2002
INVENTOR(S)   : Georges Boussignac It is certified that error appears in the above-identified patent and that said Letters Patent is hereby corrected as shown below:

<u>Title page,</u>
Item [30], Foreign Application Priority Data,
Please change the date from:
"Jan. 6. 1998"
Please enter the correct date of:
-- Jan. 6, 1997 --

Signed and Sealed this

Twenty-sixth Day of November, 2002

*Attest:*

*Attesting Officer*

JAMES E. ROGAN
*Director of the United States Patent and Trademark Office*